United States Patent [19]
Pfoslgraf et al.

[11] Patent Number: 5,514,098
[45] Date of Patent: May 7, 1996

[54] CAPS FOR SEALING A CANNULA ASSEMBLY

[75] Inventors: Lanis P. Pfoslgraf, Oconomowoc; Gene T. Kyburz, Pardeeville, both of Wis.

[73] Assignee: Owens Precision Systems, Inc., Oak Creek, Wis.

[21] Appl. No.: 221,360

[22] Filed: Mar. 31, 1994

Related U.S. Application Data

[63] Continuation-in-part of Ser. No. 13,763, Feb. 4, 1993, Pat. No. 5,312,362.

[51] Int. Cl.⁶ .................................................. A61M 5/78
[52] U.S. Cl. ............................................ 604/167; 604/256
[58] Field of Search ............................ 604/164, 167, 604/256, 264

[56] References Cited

U.S. PATENT DOCUMENTS

| | | | |
|---|---|---|---|
| 3,853,127 | 12/1974 | Spademan | 128/214.4 |
| 3,989,049 | 11/1976 | Yoon | 128/326 |
| 3,994,287 | 11/1976 | Turp et al. | 128/6 |
| 4,013,080 | 3/1977 | Froning | 604/165 |
| 4,177,814 | 12/1979 | Knepshield | 128/348 |
| 4,261,357 | 4/1981 | Kontos | 604/167 |
| 4,430,081 | 2/1984 | Timmermans | 604/167 |
| 4,655,752 | 4/1987 | Honkanen et al. | 604/167 |
| 4,809,679 | 3/1989 | Shimonaka et al. | 604/167 |
| 4,909,798 | 3/1990 | Fleischhacker | 604/167 |
| 4,991,629 | 2/1991 | Ernesto et al. | 604/256 |
| 5,009,391 | 4/1991 | Steigerwald | 604/167 |
| 5,009,643 | 4/1991 | Reich et al. | 604/167 |
| 5,041,095 | 8/1991 | Littrell | 604/167 |
| 5,092,846 | 3/1992 | Nishijima | 604/165 |
| 5,098,393 | 3/1992 | Amplatz et al. | 604/167 |
| 5,104,383 | 4/1992 | Shichman | 604/167 |
| 5,112,321 | 5/1992 | Hiltebrandt | 604/167 |
| 5,114,408 | 5/1992 | Fleischhake | 604/167 |
| 5,122,122 | 6/1992 | Allgood | 604/174 |
| 5,141,498 | 8/1992 | Christian | 604/167 |
| 5,147,305 | 9/1992 | Nakamura et al. | 604/256 |
| 5,180,373 | 1/1993 | Green et al. | 604/167 |
| 5,273,545 | 12/1993 | Hunt et al. | 604/256 |

FOREIGN PATENT DOCUMENTS

0344907A2  12/1989  European Pat. Off. .

*Primary Examiner*—John G. Weiss
*Attorney, Agent, or Firm*—Whyte Hirschboeck Dudek

[57] ABSTRACT

A cannula cap for sealing a cannula assembly during insufflatory surgery, the cap comprising an endwall made of elastomeric material and a sidewall. The cap is sized and configured to fit to the instrument entrance of a cannula in a relative gas-tight relationship. The endwall of the cap may be apertured to permit entry and exit of a trocar or other surgical instrument without significant interruption of the seal. Another embodiment provides an adaptor cap also comprising an endwall made of an elastomeric material and a sidewall, the adaptor cap arranged to be fitted to the cannula cap for temporary insertion and withdrawal of instruments of relatively small diameter without removal of the cannula cap.

18 Claims, 3 Drawing Sheets

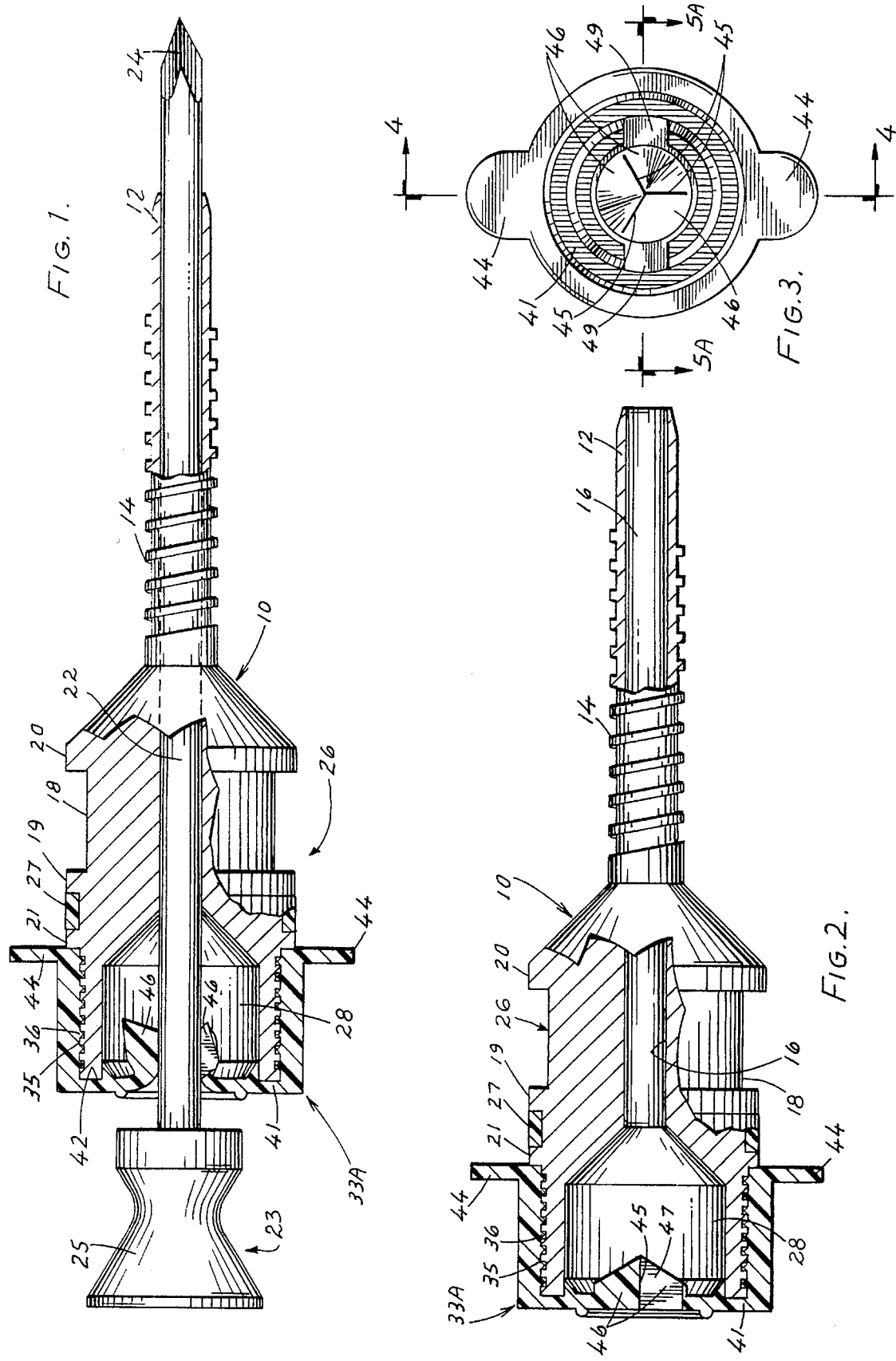

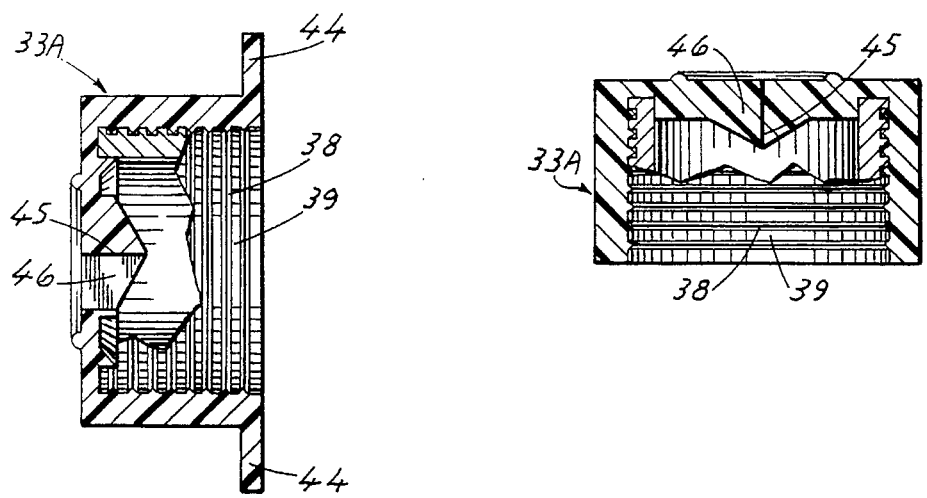
FIG. 4.
FIG. 5A
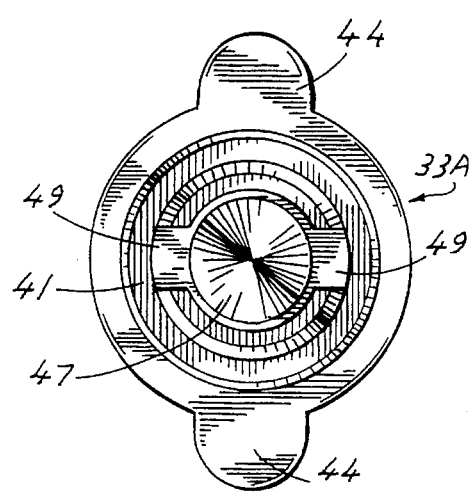
FIG. 6.
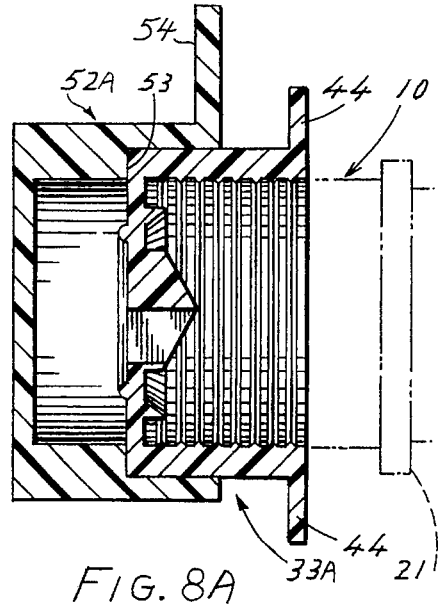
FIG. 8A

CAPS FOR SEALING A CANNULA ASSEMBLY

CROSS-REFERENCE TO RELATED APPLICATION

This application is a continuation-in-part of application Ser. No. 08/013,763, filed Feb. 4, 1993 now U.S. Pat. No. 5,312,362.

BACKGROUND OF THE INVENTION

1. Field of the Invention

The present invention relates to a cannula assembly used in insufflatory surgery. In one aspect, the invention relates to a cannula cap for sealing a cannula assembly while in another aspect, the invention relates to a adaptor cap for use in combination with the cannula cap.

2. Background of the Invention

Various types of cannula assemblies have been provided with valves for maintaining a certain gas pressure in a body cavity during insufflatory surgery. Insufflatory surgery involves filling a body cavity with pressurized gas to maintain the cavity under a certain predetermined pressure. A conventional technique of performing the surgery is to first puncture the skin in a predetermined region of the body cavity with a needle including a stylet, and introducing an insufflatory gas into the body cavity. Once pressurized, one or more cannula assemblies are inserted into the body cavity at predetermined locations (other than that at which the insufflatory gas is introduced).

A trocar is inserted into the bore of the cannula with its sharpened end extending from the distal end of the cannula. The sharpened end of the trocar is used to enable the distal end of the cannula to enter the body cavity. The trocar is then removed from the cannula, and surgical instruments inserted through the cannula to perform required endoscopic procedures. Because the body cavity is under pressure, escape of the insufflatory gas must be prevented during insertion of the instruments and the performance of the surgical procedure.

The art teaches various types of cannula assemblies provided with valves for maintaining gas pressure in the body cavity when the trocar or other surgical instruments are inserted and removed from the cannula.

U.S. Pat. No. 4,177,814 discloses a self-sealing cannula which maintains insufflation pressure in a body cavity by means of a slotted elastomeric valve positioned in a valve seat with the slot disposed over the cannula valve passage. Separate means are provided to compress the valve against a valve seat to seal the slot or slots.

U.S. Pat. No. 3,853,127 discloses a certain type of perforation formed in an elastic sealing member.

U.S. Pat. No. 3,994,287 discloses an assembly wherein gas pressure is maintained by means of a flexible ring having an aperture positioned within an annular valve seat. A collar is placed over the ring to seal the sidewalls of the valve seat. Since the disclosed assembly loses it seal when the surgeon removes the instrument, other sealing means must be provided to maintain gas pressure.

U.S. Pat. No. 3,989,049 discloses a trumpet valve to maintain pressure. The valve must be manually regulated by the surgeon while removing the trocar and replacing it with another instrument, such as a laparoscope.

U.S. Pat. No. 5,041,095 discloses a hemostasis valve to prevent blood leakage. This valve assembly utilizes a snap-on cap which houses at least a pair of separate discs, each having slots for receiving a catheter to prevent backflow of blood.

U.S. Pat. No. 5,092,846 discloses a device for introducing a catheter into a body for diagnosis or treatment, as in the case of a vascular balloon catheter.

U.S. Pat. No. 5,104,383 discloses a seal for use with a cannula assembly. This disclosure is directed principally to a stabilizer plate to limit the eccentric movement of an instrument relative to the seal which might otherwise inadvertently break the seal.

U.S. Pat. No. 5,114,408 discloses a hemostasis valve formed of a longitudinally extended valve housing. An apertured cap is provided for enclosing a first opening of the housing. The cap permits insertion of a catheter.

U.S. Pat. No. 5,122,122 discloses a trocar sleeve provided in a relatively complicated assembly requiring an expanded end of the trocar sleeve in abutting relationship with the inner surface of the abdominal cavity.

Patent Publication 0 334 907 A2 discloses a particular configuration of slits formed in a self-sealing gasket for a catheter.

OBJECTS OF THE INVENTION

One of the objects of the present invention is to provide a cannula assembly having positive sealing during entry, use, substitution and withdrawal of surgical instruments of different sizes and configurations during the performance of a surgical procedure.

Another object of the invention is to provide a cannula cap made of an elastomeric material, such as silicone, which has an inner periphery substantially conforming to the outer periphery or rim of the instrument entrance of a cannula such that the former engages the latter in a relatively gas-tight seal, i.e. a seal through which little, if any, of the inflating gas escapes.

Another object of the invention is to provide a cannula cap comprising (i) an elastomeric endwall through which instruments can be inserted, used and removed while maintaining a relatively gas-tight seal, and (ii) a sidewall of a relatively hard, nonelastic material, such as a rigid plastic, which has an inner periphery designed to engage the outer periphery of the instrument entrance of the cannula by any conventional means, e.g. screw threads, compression fit, twist and lock (similar to that used on vials for pharmaceuticals, etc., in a substantially gas-tight seal.

Another object of the present invention is to provide a single sealing member for a cannula assembly which eliminates the need for an additional compressing retainer member requiring machined threads and other machined surfaces to receive and compress a sealing valve.

Another object of this invention is to provide a cannula configuration which permits several variations of gas-sealing caps or valves adaptable for use with inserted instruments of varying diameters and configurations.

Still another object of this invention is to provide an adaptor cap which can be fitted to the external surface of and used in combination with a cannula cap, the endwall of the adaptor cap designed for receiving in a relatively gas-tight manner an instrument of small diameter (relative to other instruments that may be inserted into the cannula during a surgical procedure) thus enabling use of smaller diameter instruments without requiring removal of the cannula cap.

SUMMARY OF THE INVENTION

The objects of this invention are accomplished by the provision of a cannula cap, alone or in combination with an adaptor cap, for use with a cannula assembly. The assembly comprises a cannula with an elongated sleeve defining a through bore for receiving various surgical instruments, including a trocar for initially piercing into an operative body cavity which is to be maintained under gas pressure during the surgical procedure. The trocar enters and exits the cannula through an elastomeric, typically apertured endwall of the valve or cannula cap enclosing the instrument entrance of the cannula. The instrument entrance of the cannula can be of any shape.

In one embodiment of this invention, the outer surface of the instrument entrance of the cannula is in the shape of a cuplike enlargement of the elongated sleeve to provide, among other things, a fingergrip surface, and includes a series of axially-spaced, alternating lands and grooves. The grooves and lands are adapted to receive matching lands and grooves formed on the inner surface of one embodiment of the cannula cap, here a cap with both an elastomeric endwall and sidewall, for removably fastening and sealing the cap to the enlarged cannula portion. The endwall of the cannula cap in this and other embodiments may be apertured, preferably in the form of a Y-shaped slit which extends radially from the center of the cap. The aperture is adapted for the insertion and removal of surgical instruments during an insufflatory surgical procedure without loss of gas pressure.

In another embodiment of this invention, the elastomeric endwall of the cannula cap may be formed without an aperture. In this embodiment, the endwall may be pierced by a sharp-pointed trocar as the trocar is inserted into the cannula passage. In other embodiments, the endwall of the cannula cap may be apertured to specifically accommodate an instrument of a particular diameter, e.g. 5, 6, 10 and 12 mm diameter instruments, or apertured to accommodate instruments of different diameters or sizes. In practice, nonapertured cannula caps are used to accommodate relatively small instruments, such as a 3 mm needle, while apertured cannula caps are used to accommodate larger instruments, e.g. 8 mm or larger diameter instruments.

In another embodiment of this invention, the cannula cap comprises an elastomeric endwall and a rigid sidewall. The endwall, or at least that portion of the endwall through which an instrument is inserted, comprises an elastomeric material, e.g. silicone, which like the endwall of the cannula caps in the other embodiments of this invention forms a relatively gas-tight seal with the inserted instrument. The rigid sidewall comprises any suitable material, e.g. metal, rigid plastic, etc., that can engage the entry portion of the cannula in a gas-tight seal. This engagement can take any suitable form, e.g. screw threads, compression fit, a twist and lock mechanism, and the like, with or without a sealing aid such as silicone grease.

Another embodiment of the invention takes the form of an adaptor cap, typically an elastomeric adaptor cap, formed with an inner periphery (typically circular in shape) arranged to fit relatively tightly to the outer periphery (also typically circular in shape) of the cannula cap. The adaptor cap may be similar in construction to the cannula cap, i.e. its entire construction can be from an elastomeric material, or it can comprise an elastomeric endwall and rigid sidewall. The fit of the adaptor cap to the cannula cap is also similar to the fit of the cannula cap to the cannula, e.g. a stretch or snap fit, a screw fit, etc.

The adaptor cap permits a surgeon, who has begun the surgery with the cannula cap with, for instance, a slitted aperture for accommodating a 12 mm instrument to temporarily use a 5 mm instrument without significant gas leakage. The surgeon merely fits an adaptor cap to, typically over, the previously seated 12 mm cannula cap, and then inserts the smaller diameter instrument through the endwall of both caps. When through with the smaller diameter instrument, the adaptor cap can be removed from the cannula cap, along with the smaller 5 mm instrument, while the seal between the cannula cap and cannula remains intact. Prior procedures required the surgeon to either replace the cannula cap apertured for a 12 mm instrument with a cannula cap apertured for a 5 mm instrument with consequent loss of gas pressure, or to insert a special 12 mm diameter tube into the 12 mm slotted opening for subsequent insertion of a 5 mm instrument.

In yet another embodiment of this invention, the cannula cap and the adaptor cap are permanently joined to one another as an integral, one-piece unit.

These and other objects and features of the present invention will become more fully apparent from the following description and appended claims taken in connection with accompanying drawings.

BRIEF DESCRIPTION OF THE DRAWINGS

FIG. 1 is a side perspective of one embodiment of a self-sealing cannula assembly in accordance with this invention, shown with an associated trocar in its extended position and with certain parts being broken away and shown in longitudinal section to illustrate certain features of the present invention;

FIG. 2 is another side perspective, similar to FIG. 1, with the associated trocar removed from the cannula and also with certain parts being broken away and shown in longitudinal cross-section;

FIG. 3 is a bottom view looking interiorly of the elastomeric cannula cap of FIGS. 1 and 2 when the cap is removed from the cannula;

FIG. 4 is a longitudinal cross-sectional view of the cannula cap removed from the cannula and taken along lines 4—4 of FIG. 3;

FIG. 5A is a longitudinal cross-section view of the cannula cap removed from the cannula and taken along lines 5—5 of FIG. 3;

FIG. 6 is a bottom view of an elastomeric cannula cap removed from the cannula and illustrating a nonapertured embodiment of the cap;

FIG. 8A is a longitudinal cross-sectional view of an elastomeric cannula cap fitted directly to lands and grooves formed in the outer circumference of an enlarged portion of a cannula (shown here in phantom line), and further being fitted with an elastomeric adaptor cap for providing an interim seal during temporary insertion and removal of a surgical instrument of relatively small diameter into the aperture of the cannula cap having an aperture adopted to initially receive a trocar and/or other surgical instruments of larger diameter.

DETAILED DESCRIPTION OF PREFERRED EMBODIMENT

Figure 5B:
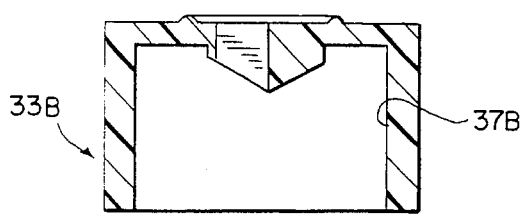
FIG. 5B is the cannula cap of FIG. 5A but without lands and grooves about its interior sidewall surface.

With reference to the drawings and especially to FIGS. 1–5, inclusive, there is shown a self-sealing cannula assembly in accordance with the present invention. The cannula comprises body 10 and elongated sleeve 12. Sleeve 12 is connected to body 10 by conventional means, such as threading, force-fit with or without crimping, etc., or each can be an integral section of a molded or machined single piece of manufacture. As shown, sleeve 12 is formed with axially spaced threads or other radially extending projections 14 as one means for retaining the cannula in a body cavity after the former is inserted into the latter.

Body 10 includes a bore which extends longitudinally through its entire length. Passage 16 in sleeve 12 and cuplike chamber 28 communicate with one another to define the bore. The material of body 10 may be stainless steel, or a high temperature thermoplastic or thermoset resin, or any other material which will be acceptable for sterilization by gas, autoclave, or any other form of sterilization.

Fingergrip portion 18 of expanded diameter is defined by axially spaced, radial flanges 19 and 20 to facilitate easy grasping and manipulation by an operating surgeon. Seated between flange 19 and coaxially spaced auxiliary flange 21 is annular band of color-coded material 27, which may comprise a silicone coating of a color chosen to match the color of cannula cap 33A.

Passage 16 in sleeve 12 is arranged to receive shaft portion 22 of trocar 23 having a sharp distal end portion 24 and terminating into handle 25. The cannula assembly may be utilized with various types of pointed or blunted trocars, and it is arranged for receiving various surgical instruments upon removal of trocar 23 from body 10.

Body 10 is formed at its rearward end 26 to provide cuplike chamber 28 that tapers forwardly to terminate in internal passage 16 of body 10. Cuplike chamber 28 provides a cavity for receiving inwardly projecting portions or flaps 46 of elastomeric cannula cap 33A arranged to enclose the open end of chamber 28 (i.e., the instrument entrance of cannula).

With particular reference to cap 33A and enlarged rearward end portion 26 of body 10, elastomeric cap 33A is formed to provide a self-sealing relationship with body 10. In the embodiment of FIGS. 1 and 2, this self-sealing relationship is accomplished by forming a series of alternating, radially extending lands 35 and grooves 36 on the outer circumference of rearward end 26 of body 10. Axially spaced lands 35 and grooves 36 of body 10 are arranged to received respective registering grooves 38 and lands 39 formed on the internal circumferential surface of cap 33A (see FIG. 5A).

In the embodiment shown in FIG. 5B, cap 33B is sized to engage tightly the outer circumference of rearward end 26 of body 10 to form a gas-tight seal without the presence of lands and grooves on either the outer circumference of rearward end 26 or on internal sidewall circumferential surface 37B of cap 33B. In this embodiment, these surfaces are typically smooth, and cap 33B tightly engages rearward end 26 by simply stretching the former over the latter.

Figure 5C:
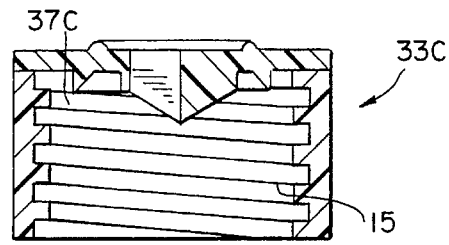
FIG. 5C is the cannula cap of FIG. 5A but with screw threads about its interior sidewall surface.

In the embodiment shown in FIG. 5C, sidewall 37C of cap 33C is made of a rigid material, e.g. any rigid plastic exhibiting the necessary characteristics for use in surgical applications, and it is equipped with screw thread 15 on its internal circumferential surface which are designed to engage in a gas-tight seal complimentary screw groove (not shown) on the outer circumference of rearward end 26.

In all the figures except FIG. 5C, caps 33A and 33B are formed of an elastomeric material, such as silicone, which permits a "snap or stretch fit" when it is fitted onto the rearward end of body 10 until the interior, annular flat surface portion of endwall 41 abuts outermost marginal edge surface 42 of body 10. These caps form a gas-tight seal with body 10 when the former are seated on the latter. Radially extending, oppositely disposed, ears 44 are integrally formed with and extend radially from cap 33A to provide fingergrips for easy application and removal of cap 33A to and from cannula body 10. In those embodiments in which the cannula cap is secured to the cannula body in a manner other than a snap or stretch fit, e.g. in a threading engagement, then the ears are usually omitted.

Since cannula assemblies are conventionally manufactured and sold in various sizes, the present invention further contemplates the provision of color-coding means to assist in matching cannula body 10 of given size with a cap of matching size. As illustrated in the views of FIGS. 1 and 2, there is provided an area defined by axially spaced flanges 19 and 21. Band 27 is selected of a material to match the color of the cap having an aperture matching that of the distal end of elongated sleeve 12. Thus, during a surgical procedure there may be cannula assemblies chosen by the surgeon to receive trocars or other instrument of a particular diameter which may vary in size depending on the instrument used. Color-coded band 27 will readily assist in selecting a cap of the same color coding to insure a proper fit between the matching components. Band 27 may be formed by depositing a layer of silicone of selected color between flanges 19 and 21. Other color-coding means, including adhesively affixed separately fabricated color-coded bands, may also be used.

With particular reference to FIGS. 3–5A, inclusive, it will be noted that, for receipt of trocar 23, as illustrated in FIG. 1, and of later inserted surgical instruments (not shown) upon removal of trocar 23, cannula cap 33A may be apertured in the form of Y-shaped slit 45. This slit defines valve or cannula cap flaps 46 which are further defined by an inwardly projecting convex, pyramidal-like portion or area 47 for providing added strength to endwall 41 of cap 33A. Cap 33A does not require any additional compression type fittings, but may be made as one integrally formed unit of elastomeric material, which is both resiliently flexible and self-sealing because of its elasticity which provides the tight fit between it and body 10. Additional lateral strength may be provided to endwall 41 by means of the diametrically opposed bridging portions 49 (see FIG. 3), which are integrally molded into cannula cap 33A.

As seen from the illustrations of FIGS. 1 and 2, trocar 23 may be inserted in passage 16 of cannula body 10 with the surgeon grasping handle 25 thereof with one hand and fingergrip portion 18 of body 10 with the other hand, in this manner initially piercing the patient's skin and entering the gas-filled body cavity of the patient. The radially extending projections 14 on sleeve 12 of body 10 provide additional retention of sleeve 12 after the cannula has been inserted into the gas-filled body cavity.

With reference to FIG. 1, the insertion of trocar 23 will cause flaps 46 to extend into chamber 28. The elastomeric material of flap portions 46 will provide the needed self-sealing characteristics for retention of the required gas pressure in the body cavity of the patient. Withdrawal of trocar 23, leaving the cannula body devoid of any inserted instruments, as shown in FIG. 2, will permit flaps 46 to retract to their original configuration for maintenance of the required seal and with cannula sleeve 12 remaining in the pressurized body cavity. Obviously, additional instruments may be inserted into slit 45 of body 10 for usual surgical endoscopic procedures. These instruments may be inserted and removed as needed without interruption of the desired sealing characteristics.

Figure 6A:
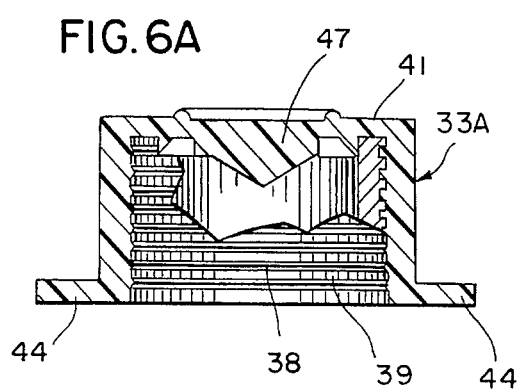
FIG. 6A is a side view of FIG. 6.

With respect to the embodiments described in FIGS. 1–5C, the aperture formed by slit 45 is intended to accommodate relatively large diameter instruments, such as those having diameters in excess of 7 mm. Should the surgeon require insertion of smaller instruments, such as a 5 mm diameter instrument, endwall 41 of cap 33A is preferably nonapertured (as shown in FIG. 6A). In such circumstances, the endwall is usually thin relative to the endwalls of the slitted embodiments.

Reference is now made to FIGS. 7A–8B and adaptor caps 52A–C. Instances occur in which a surgeon working on a insufflatory procedure may wish to use instruments of varying diameter. Those embodiments of the present invention which include the use of an adaptor cap permit the surgeon this flexibility.

In such circumstances, an adaptor cap, usually a one-piece construction of an elastomeric material (e.g. silicone) but which can also be a multipiece construction comprising an elastomeric endwall connected to a rigid sidewall, can be temporarily fitted to a cannula cap which has been previously applied and seated on the rearward portion of the cannula body. The adaptor cap may be apertured or nonapertured, its surface textured or smooth, and free of or equipped with "ears" or other means for assisting in its application to and removal from the cannula cap.

Figure 7A:
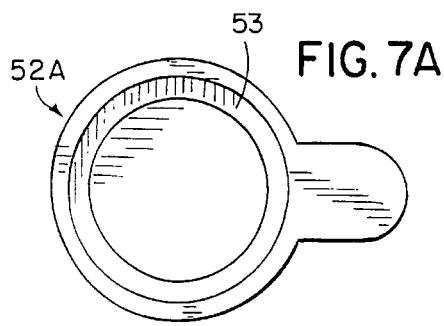
FIG. 7A is a bottom view looking interiorly of one embodiment of an elastomeric adaptor cap.
Figure 7B:
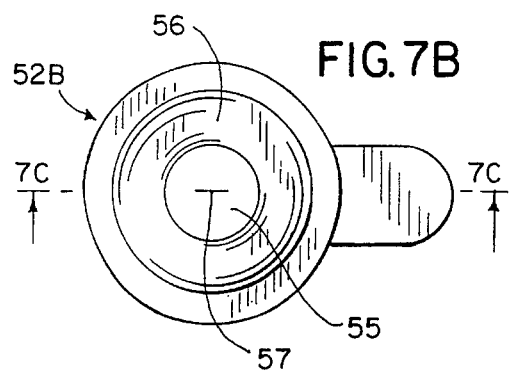
FIG. 7B is a top view of the elastomeric adaptor cap of FIG. 7A here including a fold of excess elastomeric material.
Figure 7C:
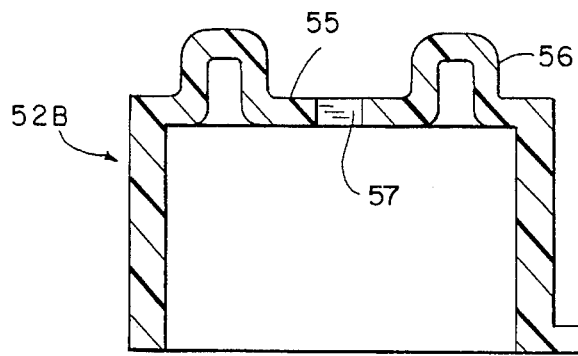
FIG. 7C is a longitudinal cross-sectional view of the elastomeric adaptor cap of FIG. 7B.

In a preferred embodiment of this invention and as shown in FIGS. 7B and 7C, adaptor cap 52B is a one-piece construction of elastomeric material, and its endwall 55 contains ripple or fold 56 of excess elastomeric material. The placement of this ripple on endwall 55 can vary to convenience, but typically it is located as a circle or ring about the center of endwall 55 (here shown with aperture 57). This excess material assists in maintaining the relatively gas-tight seal between the adaptor cap endwall and the instrument as the surgeon manipulates the latter during an operative procedure. In other embodiments not shown, the ripple can extend onto the sidewall of the adaptor cap. FIG. 7A illustrates a nonapertured adaptor cap.

Figure 8B:
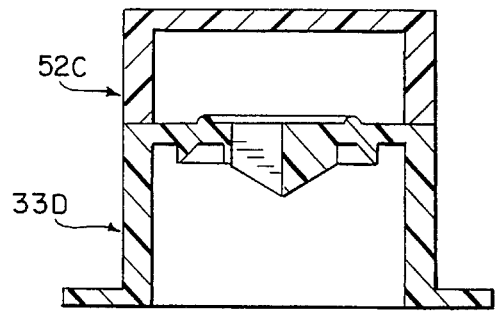
FIG. 8B is a longitudinal cross-sectional view of another embodiment of a cannula cap in combination with an adaptor cap, here the latter fused to the former.

The adaptor cap is preferably made of the same material as the cannula cap and in one embodiment, it may be fitted in "piggyback" relationship to the exterior endwall of the cannula cap, as shown in FIG. 8A. In another embodiment, cannula cap 33A and adaptor cap 52C can be permanently joined to one another in this piggyback relationship by any suitable technique, e.g. through the action of an adhesive, heat sealing, molding, etc., to form an integral, one-piece unit as shown in FIG. 8B. In those embodiments in which the sidewalls of the adaptor and cannula caps are rigid, each can be equipped with complimentary screw threads or other joining means which permit the joining of one to the other in a relatively gas-tight seal.

In certain embodiments (e.g. FIG. 8A), shoulder portion 53 acts as an abutment for stopping the insertion of adaptor cap 52A relative to cannula cap 33A. Adaptor cap ear 54 may also be provided to facilitate application and removal of adaptor cap 52A from cannula cap 33A.

After the surgeon finishes his or her procedure using the smaller diameter instrument, both the smaller diameter instrument and adaptor cap 52A may be removed to provide for entry of an instrument of larger diameter. The gas seal is not broken during this removal.

The cannula assemblies, cannula caps and adaptor caps described above provide many advantages over those known in the art. These assemblies and caps permit the temporary use of surgical instruments of relatively small diameter after an initial insertion of a trocar or other instruments of relatively large diameter, e.g. approximating that of the trocar.

While this invention has been described in detail and with reference to the Figures, this detail and reference is for the purpose of illustration only and is not to be construed as a limitation upon the scope of the invention as described in the following claims.

What is claimed is:

1. An apparatus for sealing a cannula during an insufflatory surgical procedure, the cannula comprising an entrance defined by a marginal end surface for receiving surgical instruments, the apparatus comprising:

a cannula cap comprising a sidewall and at least a partially elastomeric endwall for enclosing the entrance, the elastomeric endwall having an inwardly projecting convex area, the cannula cap adapted for engagement with the entrance of the cannula so as to provide a relatively gas-tight seal; and an adapter cap having a sidewall and an endwall, the endwall being substantially planar and perpendicular to the sidewall and comprised at least partially of an elastomeric material, the adapter cap sealingly engaged to the cannula cap and free of engagement with the cannula, the adapter cap allowing the insertion of a relatively smaller surgical instrument than that capable without the adapter cap while maintaining the relative gas-tight seal.

2. The apparatus of claim 1 in which the sidewall of the cannula cap has an inner periphery substantially conforming to the outer periphery of the entrance of the cannula.

3. The apparatus of claim 2 in which the cannula cap is sized and configured to engage the outer periphery of the entrance of the cannula, the entrance configured as an enlarged, circular cuplike chamber.

4. The apparatus of claim 3 in which the cannula cap is a one-piece construction of an elastomeric material.

5. The apparatus of claim 4 wherein the cannula cap further comprises a bridging, integral support element projecting inwardly from the endwall of the cannula cap and radially extending from the center of the endwall of the cannula cap to the sidewall of the cannula cap to provide additional rigidity to the endwall.

6. The apparatus of claim 1 in which the endwall of the cannula cap is apertured for receiving a surgical instrument.

7. The apparatus of claim 6 in which the aperture in the cannula cap endwall is a Y-shaped slit, the legs of the Y located on the inwardly projecting convex area and projecting radially outwardly from the center of the convex area.

8. The apparatus of claim 5 in which the cannula cap endwall is nonapertured.

9. The apparatus of claim 1 in which the inner periphery of the cannula cap contains a plurality of alternately, axially spaced grooves and lands adapted to mate in sealing engagement with corresponding alternately axially spaced lands and grooves on the outer periphery of the entrance of the cannula.

10. An apparatus for sealing an end of a cannula, said apparatus comprising: an adaptor cap and a cannula cap, the cannula and adaptor caps each comprising a sidewall and at least a partially elastomeric end wall, the partially elastomeric end wall of the cannula cap having an inwardly projecting convex surface, the adaptor cap sidewall attached to the cannula cap end wall effectively extending the sidewall of the cannula cap thereby forming a relatively tight gas-sealing relationship with the cannula cap, and the end wall of the adaptor cap adapted for receiving a surgical instrument in a relatively tight gas-sealing engagement.

11. The apparatus of claim 10 in which the adapter cap endwall comprises a ripple of excess elastomeric material.

12. The apparatus of claim 11 in which the adapter cap is a one-piece construction of an elastomeric material.

13. The apparatus of claim 12 in which the elastomeric material is a silicone.

14. The apparatus of claim 12 wherein the adapter cap further comprises a shoulder about the inner periphery of the adapter cap sidewall such that the shoulder engages a portion of the exterior surface of the endwall of the cannula cap.

15. A cannula cap assembly for sealing a cannula used during surgical procedures, the cannula comprising an entrance defined by a marginal end surface for receiving surgical instruments, the cap assembly comprising:

A. a first cannula cap comprising:
   (1) a rigid first sidewall;
   (2) a first end wall extending from said first sidewall, said first end wall comprising at least partially of an elastomeric material different than the material of the rigid first sidewall;
   (3) an inwardly projecting, pyramidal-like portion extending from said first end wall, said pyramidal-like portion formed of elastomeric material and having an inwardly projecting convex area with a slit therein to allow the insertion of a surgical instrument in a substantially sealed arrangement;

B. a second cannula cap comprising:
   (1) a second sidewall; and
   (2) a second end wall extending from said second sidewall, said second end wall comprising at least partially of an elastomeric material and adapted for receiving a smaller surgical instrument in a relatively tight, gas-sealing engagement;

C. wherein said second cannula cap is fitted to said first cannula cap to form a substantially gas-tight seal.

16. The cannula cap assembly of claim 15 wherein the substantially gas-tight seal formed by the second cannula cap fitted to the first cannula cap is formed between the first rigid sidewall of the first cannula cap and the second sidewall of the second cannula cap.

17. A cannula cap assembly for sealing a cannula used during surgical procedures, the cannula comprising an entrance defined by a marginal end surface for receiving surgical instruments, the cap assembly comprising:

A. a first cannula cap comprising:
   (1) a rigid first sidewall;
   (2) a first end wall extending from said first sidewall, said first end wall comprising at least partially of an elastomeric material different than the material of the rigid first sidewall; and
   (3) a first inwardly projecting, pyramidal-like portion extending from said first end wall, said first pyramidal-like portion formed of elastomeric material and having at least two cannula cap flaps to allow the insertion of a surgical instrument in a substantially sealed arrangement;

B. a second cannula cap comprising:
   (1) a second sidewall; and
   (2) a second end wall extending from said second sidewall, said second end wall comprising at least partially of an elastomeric material and adapted for receiving a smaller surgical instrument in a relatively tight, gas-sealing engagement;

C. wherein said second cannula cap is fitted to said first cannula cap to form a substantially gas-tight seal.

18. The cannula cap assembly of claim 12 wherein the substantially gas-tight seal formed by the second cannula cap fitted to the first cannula cap is formed between the first rigid sidewall of the first cannula cap and the second sidewall of the second cannula cap.

* * * * *